(12) United States Patent
Zhang et al.

(10) Patent No.: US 12,090,144 B2
(45) Date of Patent: Sep. 17, 2024

(54) PHOTOCURABLE HYDROGEL LOADED WITH VH298-MODIFIED EXOSOME AND METHOD OF PREPARATION AND USE THEREOF

(71) Applicant: Chinese PLA General Hospital, Beijing (CN)

(72) Inventors: Cuiping Zhang, Beijing (CN); Yaxi Wang, Beijing (CN); Kui Ma, Beijing (CN); Xiaobing Fu, Beijing (CN)

(73) Assignee: Chinese PLA General Hospital, Beijing (CN)

( * ) Notice: Subject to any disclaimer, the term of this patent is extended or adjusted under 35 U.S.C. 154(b) by 28 days.

(21) Appl. No.: 17/876,811

(22) Filed: Jul. 29, 2022

(65) Prior Publication Data

US 2024/0033253 A1    Feb. 1, 2024

(51) Int. Cl.
| | |
|---|---|
| *A61K 31/427* | (2006.01) |
| *A61K 9/06* | (2006.01) |
| *A61K 9/127* | (2006.01) |
| *A61P 17/02* | (2006.01) |

(52) U.S. Cl.
CPC .............. *A61K 31/427* (2013.01); *A61K 9/06* (2013.01); *A61K 9/127* (2013.01); *A61P 17/02* (2018.01)

(58) Field of Classification Search
CPC ........ A61K 31/427; A61K 9/06; A61K 9/127; A61P 17/02
See application file for complete search history.

(56) References Cited

PUBLICATIONS

Wu et al. (Preservation of Small Extracellular vesicle in Gelatin Methylacryloyl Hydrogel through Reduced Particles Aggregation for Therapeutic Applications), International Journal of Nanomedicine, Nov. 30, 2021.*

* cited by examiner

*Primary Examiner* — Zohreh A Fay
(74) *Attorney, Agent, or Firm* — Bay State IP, LLC

(57) ABSTRACT

The present disclosure provides a photocurable hydrogel loaded with VH298-modified exosome and a method of preparation and use thereof, belonging to the technical field of medical materials. In the present disclosure, an engineered exosome (VH-EVs) is prepared by combining an exosome with VH298, a hypoxia-inducible factor 1 alpha (HIF-1α) stabilizer; and a solid auxiliary material is loaded by a GelMA hydrogel. The material is not only conducive to sustained release of the engineered exosome, but improves angiogenesis and accelerate wound healing, showing a relatively high value for use.

20 Claims, 4 Drawing Sheets

PHOTOCURABLE HYDROGEL LOADED WITH VH298-MODIFIED EXOSOME AND METHOD OF PREPARATION AND USE THEREOF

TECHNICAL FIELD

The present disclosure belongs to the technical field of medical materials, and in particular relates to a photocurable hydrogel loaded with VH298-modified exosome and a method of preparation and use thereof.

BACKGROUND ART

Wound healing is a complex and delicate process, in which angiogenesis is a crucial link. In diabetic patients, continuous stimulation of a high-glucose environment causes vascular endothelial cell damage and accelerates aging. This may lead to impaired angiogenesis and insufficient vascularization, resulting in delayed wound healing or post-healing dysfunction. Promotion of angiogenesis as a main therapeutic target is of great importance for the healing of diabetic wounds.

Hypoxia-inducible factor 1 alpha (HIF-1α) is involved in epithelialization, angiogenesis, granulation tissue formation and wound contraction during healing. VH298 is an HIF-1α stabilizer that specifically blocks the binding of Von Hippel-Lindau (VHL) protein to the HIF-1a. However, the use of VH298 in wound healing is limited due to poor water solubility.

SUMMARY

In view of this, an objective of the present disclosure is to provide a photocurable hydrogel loaded with VH298-modified exosome and a method of preparation and use thereof. The material may solve poor water solubility of VH298, and has an effect of accelerating angiogenesis and promoting wound healing.

The present disclosure provides a method of preparation for a photocurable hydrogel loaded with VH298-modified exosome, including the following steps:

1) introducing VH298 into an exosome to obtain a VH298-modified exosome; and
2) mixing the VH298-modified exosome obtained in step 1) with a hydrogel, and conducting an ultraviolet crosslinking to obtain the photocurable hydrogel loaded with VH298-modified exosome.

In some embodiments, in step 1), a cell source of the exosome may include one or more of a stem cell, a 293 cell, a fibroblast, and an endothelial cell.

In some embodiments, in step 2), a method for introducing the VH298 into the exosome may specifically include: mixing a PBS solution of the exosome with the VH298, treating an obtained incubation solution by one of an electric shock method, a co-incubation method, and a cyclic freeze-thaw method, subjecting a treated incubation solution to solid-liquid separation, and collecting a solid phase; the electric shock method may include: subjecting the incubation solution to an electric shock in a square wave mode at a voltage of 1,000 V and a pulse of 1 ms, with an electrode plate spacing of 0.4 cm; the co-incubation method may include: conducting incubation on the incubation solution in a water bath at 36° C. to 38° C. for 1 h to 1.2 h in the dark; the cyclic freeze-thaw method may include: treating the incubation solution in liquid nitrogen for 2 min to 3 min and then at 36° C. to 38° C. for 2 min to 3 min successively, and conducting 3 cycles of freeze-thaw treatment.

In some embodiments, the VH298-modified exosome and the hydrogel may have a volume ratio of 1:10 to 1:20; and the hydrogel may be a PBS solution including GelMA with a mass concentration of 5% to 15% and a LAP photoinitiator with a mass concentration of 0.2% to 0.3%.

In some embodiments, the ultraviolet crosslinking may be conducted at a wavelength of 405 nm for 8 sec to 12 sec.

The present disclosure further provides a photocurable hydrogel loaded with VH298-modified exosome prepared by the method of preparation.

The present disclosure further provides use of the photocurable hydrogel loaded with VH298-modified exosome in preparation of a medical material for wound vascular repair.

The present disclosure provides a photocurable hydrogel loaded with VH298-modified exosome. In the present disclosure, with the exosome as a background, the tissue repair and angiogenesis promotion effect of the exosome may accelerate angiogenesis, promoting the healing of diabetic skin wounds, and enhancing a use value of the exosome. Loading VH298 into exosome solves the poor water solubility of VH298; meanwhile, the ability of exosome is accurately improved to activate an HIF-1 a pathway exogenously and promote the angiogenesis, thereby solving the persistent wound healing caused by angiogenesis disorders in the environment of diabetes. This is expanded use of the exosome as a natural carrier for drug delivery. After combination of the VH298-modified exosome with the hydrogel, active pharmaceutical ingredients may be released continuously; moreover, the prepared photocurable hydrogel can completely fit the contour of wound, conforming to the stretching and extension of skin, with desirable water absorption and air permeability. The photocurable hydrogel loaded with VH298-modified exosome is safer and more convenient for administration, realizes the storage of exosomes in vivo, and avoids the risk of bleeding and infection caused by repeated injections. Exosomes cover the wound surface more comprehensively and evenly to reduce the waste of exosomes caused by rapid clearance in the body, which improve the bioavailability.

DETAILED DESCRIPTION OF THE EMBODIMENTS

Figure 1:
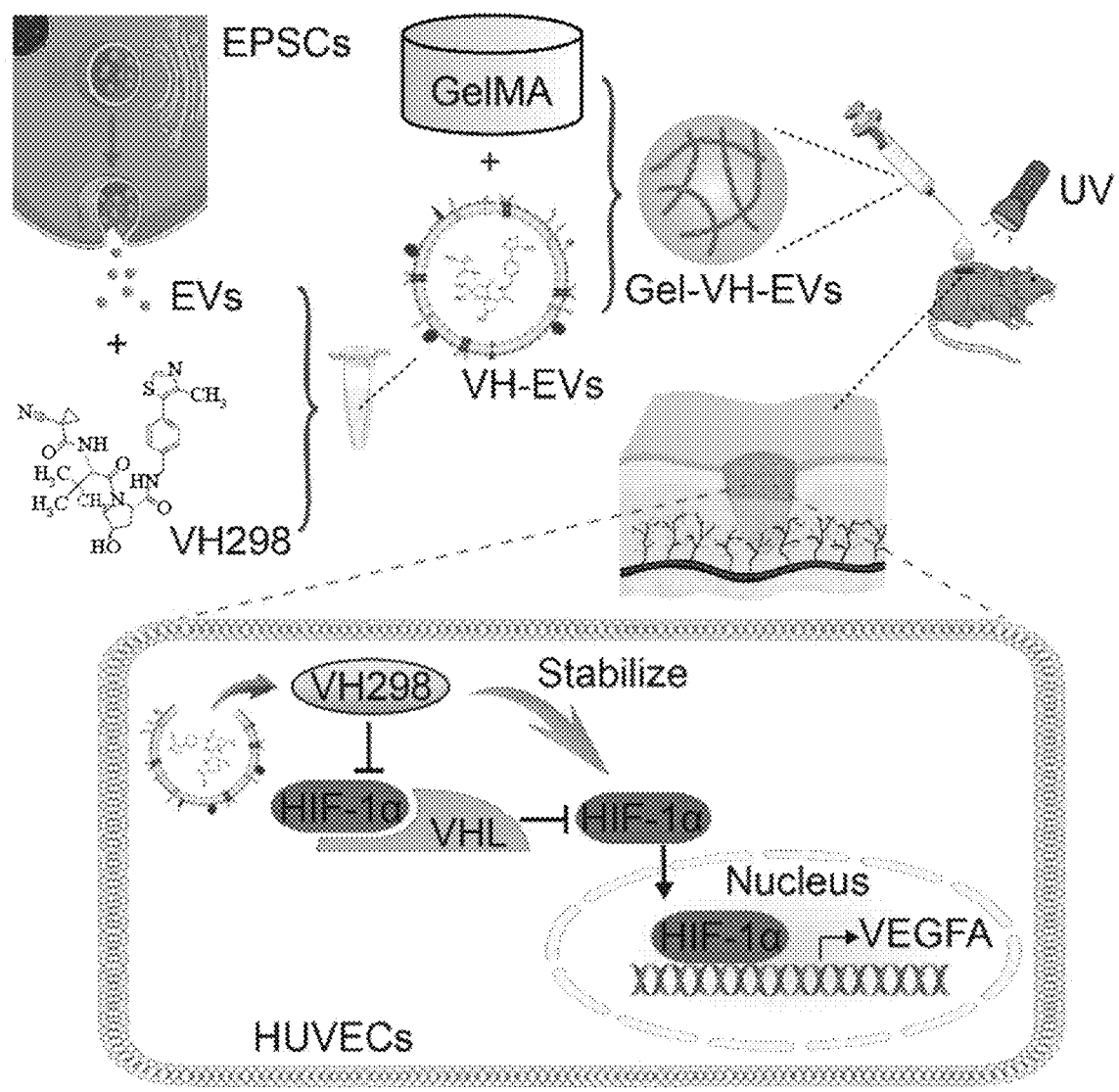
FIG. 1 shows a synthesis process of a photocurable hydrogel loaded with VH298-modified exosome, and a use process and mechanism involved.

The present disclosure provides a method of preparation for a photocurable hydrogel loaded with VH298-modified exosome, including the following steps:
1) introducing VH298 into an exosome to obtain a VH298-modified exosome; and
2) mixing the VH298-modified exosome obtained in step 1) with a hydrogel, and conducting an ultraviolet crosslinking to obtain the photocurable hydrogel loaded with VH298-modified exosome.

In the present disclosure, the VH298 has a CAS Number of 2097381-85-4, with a molecular formula of $C_{27}H_{33}N_5O_4S$. There is no special limitation on a source of the VH298, and VH298 known in the art can be used. In an example, the VH298 is purchased from MCE.

In the present disclosure, a cell source of the exosome includes one or more of a stem cell, a 293 cell, a fibroblast, and an endothelial cell. In some embodiments, the stem cells are mesenchymal stem cells. In some embodiments, a method for collecting the exosome includes the following steps: A, conducting subculture on exosome-derived cells, and continuously culturing selected cells that are in desirable condition and have a strong proliferation ability on an exosome-free serum medium for 48 h, and removing impurities to obtain a culture supernatant; B, subjecting the culture supernatant to solid-liquid separation, and collecting a solid phase to obtain the exosome. The exosome-free serum medium is a medium from which exosomes in serum are removed; in an example, the exosome-free serum used is purchased from SBI. In some embodiments, continuous culture is conducted at 37° C. In some embodiments, the impurities are removed by centrifugation. In some embodiments, the centrifugation is conducted at 10,000 g to 100,000 g. In some embodiments, the centrifugation is conducted for 30 min to 75 min.

In some embodiments of the present disclosure, the solid-liquid separation is conducted by high-speed centrifugation. In some embodiments, the high-speed centrifugation is conducted at g. In some embodiments, the high-speed centrifugation is conducted for 30 min. In some embodiments, the solid phase is resuspended in PBS, and characteristic identification and concentration detection are conducted through an exosome resuspension.

In some embodiments of the present disclosure, a method for introducing the VH298 into the exosome specifically includes: mixing a PBS solution of the exosome with the VH298, treating an obtained incubation solution by one of an electric shock method, a co-incubation method, and a cyclic freeze-thaw method, subjecting a treated incubation solution to solid-liquid separation, and collecting a solid phase; the electric shock method may include: subjecting the incubation solution to an electric shock in a square wave mode at a voltage of 1,000 V and a pulse of 1 ms, with an electrode plate spacing of 0.4 cm; the co-incubation method may include: conducting incubation on the incubation solution in a water bath at 36° C. to 38° C. for 1 h to 1.2 h in the dark; the cyclic freeze-thaw method may include: treating the incubation solution in liquid nitrogen for 2 min to 3 min and then at 36° C. to 38° C. for 2 min to 3 min successively, and conducting 3 cycles of freeze-thaw treatment. In the incubation solution, the exosome has a concentration of $1 \times 10^{10}$ particles/mL to $5 \times 10^{10}$ particles/mL; and the VH298 has a final concentration of 140 μM to 160 μM in some embodiments, preferably 150 μM. In some embodiments, the solid-liquid separation is conducted by high-speed centrifugation. In some embodiments, the solid phase is resuspended in PBS. The resuspended VH298-modified exosome has a concentration of $1 \times 10^{11}$ particles/mL to $5 \times 10^{11}$ particles/mL.

In some embodiments of the present disclosure, the VH298-modified exosome and the hydrogel have a volume ratio of 1:10 to 1:20, preferably 1:10. The hydrogel is a PBS solution including GelMA with a mass concentration of 5% to 15% and a LAP photoinitiator with a mass concentration of 0.2% to 0.3%, and in some embodiments the PBS solution includes the GelMA with a mass concentration of 10% and the LAP photoinitiator with a mass concentration of 0.25%.

In some embodiments of the present disclosure, the ultraviolet crosslinking is conducted at a wavelength of 405 nm for 8 sec to 12 sec, preferably 10 sec. The liquid hydrogel is cross-linked after UV irradiation to form a solid auxiliary material.

Based on properties of the photocurable hydrogel loaded with VH298-modified exosome to promote wound healing, the present disclosure further provides use of the photocurable hydrogel loaded with VH298-modified exosome in preparation of a medical material for wound vascular repair.

The photocurable hydrogel loaded with VH298-modified exosome and the method of preparation and the use thereof provided by the present disclosure are described in detail below in conjunction with examples, but the examples should not be construed as limiting the protection scope of the present disclosure.

Example 1

A method of preparation for a photocurable hydrogel loaded with VH298-modified exosome (Gel-VH-EVs) included the following steps:
1. Extraction of exosomes: mesenchymal stem cells were subcultured, cells with desirable state and strong proliferation ability were selected, and cultured for 48 h in an exosome-free serum medium, impurities such as cell debris were removed, and a supernatant was collected. The supernatant was centrifuged at 10,000 g for 30 min, and pellets were resuspended in PBS. Extracted exosome resuspension was characterized and concentration thereof was detected.
2. Preparation of VH298-modified exosomes (VH-EVs): am exosome PBS solution was mixed with VH298 and shaken well to obtain an incubation solution, where the exosomes had a concentration of $2 \times 10^{10}$ particles/mL, and the VH298 had a concentration of 150 NM. The incubation solution was incubated in a 37° C. water bath for 1 h in the dark. The incubation solution was centrifuged twice at 100,000 g for 75 min, and resuspended in PBS to obtain the VH298-modified exosomes with a concentration of $2 \times 10^{11}$ particles/mL.
3. Preparation of Gel-VH-EVs: a LAP photoinitiator was dissolved in PBS to obtain a 0.25% (w/v) LAP photoinitiator standard, and a GelMA lyophilized block was added at a concentration of 15% (w/v), dissolved and shaken by vortex; a mixture was put in a water bath at 50° C. for 30 min, and filtered by a 0.22 μm sterile filter in a flowing state to obtain a GelMA hydrogel liquid.

The VH298-modified exosomes prepared in step 2 were mixed with the GelMA hydrogel liquid (1:10, v/v) obtained in S302, and filtered by a 0.22 μm filter for sterilization for later use.

Figure 2:
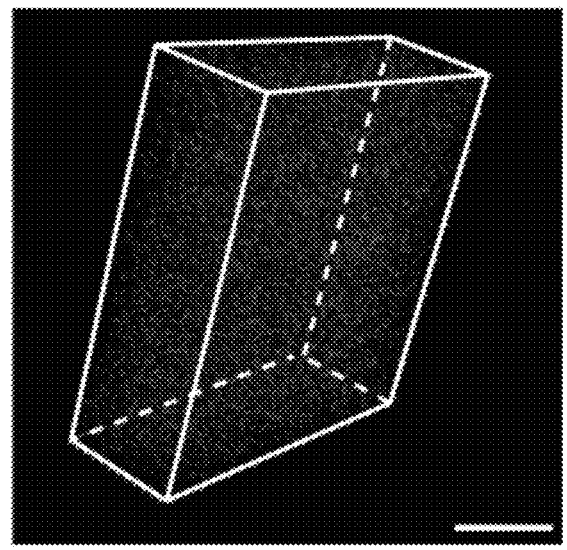
FIG. 2 shows distribution of exosomes in a Gel-VH-EVs hydrogel observed under a laser confocal microscope in Example 1.

The prepared Gel-VH-EVs were observed under a laser confocal microscope to observe the distribution of exosomes. It was seen from FIG. 2 that the exosomes were uniformly dispersed in the Gel-VH-EVs.

Example 2

Evaluation of sustained release function of the Gel-VH-EVs prepared in Example 1
1. In Vitro Evaluation:
   Co-incubation of Gel-VH-EVs and HUVECs: 50 μL of 15% Gel-VH-EVs in a mobile phase was added dropwise into small cells of a u-Slide 2×9 well cell co-culture dish, fixated and cross-linked under a light source of 405 nm wavelength, HUVECs were inoculated into other cells of the same dish, 700 μL of a serum-free DMEM medium was added to immerse the Gel-VH-EVs; an equivalent of HUVECs were inoculated into another dish, and the same amount of free VH-EVs (PKH26-labeled) as that of Gel-VH-EVs and 700 μL of the serum-free DMEM medium were added. After co-incubation for 12 h, 24 h, 48 h and 72 h, the co-incubation of Gel-VH-EVs and free VH-EVs with HUVECs was terminated at the same time. The cells were fixed, stained and photographed to observe the number of exosomes inside and outside the cells.

Figure 3:
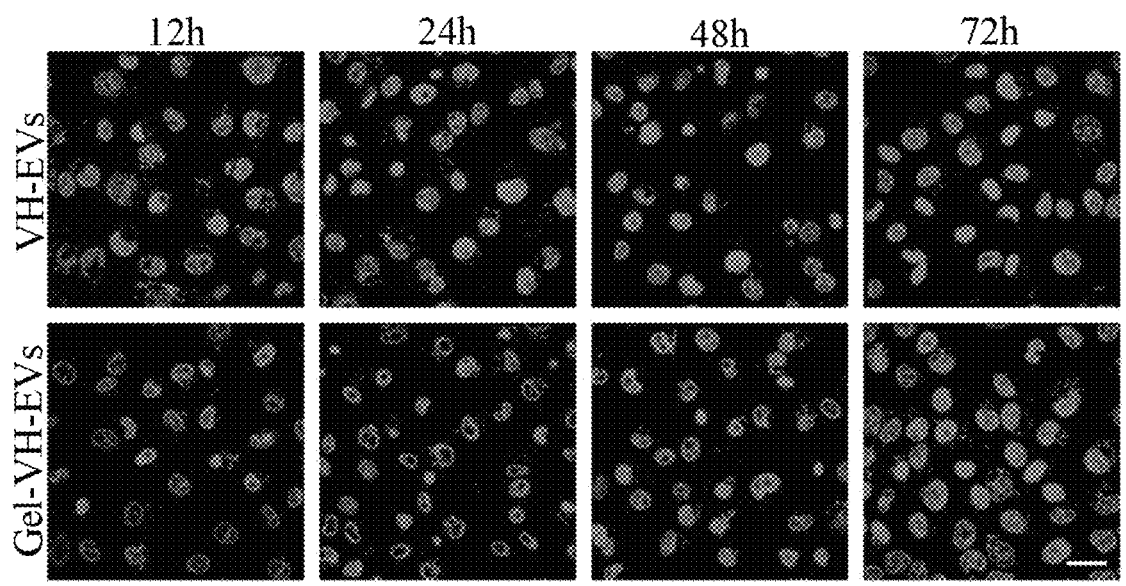
FIG. 3 shows that exosomes released by the Gel-VH-EVs hydrogel in Example 2 are internalized by vascular endothelial cells at 12 h, 24 h, 48 h and 72 h separately, with a same amount of free exosomes as a control.

However, over time, more and more VH-EVs released by Gel-VH-EVs were ingested by HUVECs, while less and less free VH-EVs gradually disappeared at 72 h (FIG. 3). This phenomenon indicates that Gel-VH-EVs can release VH-EVs slowly and for a longer time, and the released VH-EVs can be efficiently internalized by HUVECs.
2. In Vivo Evaluation:
   Establishment of Diabetic Wound Model in Mice:
   a) Anesthesia: 10 eight-week-old male diabetic mice were anesthetized by intraperitoneal injection of a 1% sodium pentobarbital solution (administered at a dosage of 0.1 mL/20 g).
   b) Operation: after the anesthesia, the hair on the back of mice were removed, two positions 1 cm from a mid-spinal line on both sides of the back of mice were marked using a trephine puncher with a diameter of 10 mm, and full-thickness resection was conducted on the marked skin.

Postoperative administration of diabetic wounds in mice: on the day of modeling, each mouse was administered to the wounds on both sides of the back, and 25 μL of PKH26-labeled VH-EVs were subcutaneously injected around the wound margin at 3, 6, 9, and 12 o'clock with a microsyringe on one side, for a total of 100 μL; the mobile phase Gel-VH-EVs containing the same amount of PKH26-labeled exosomes was added dropwise on the wounds with a syringe on the other side, and the wounds were rapidly fixated after being irradiated with a portable light source at a 405 nm wavelength for 20 sec.

Evaluation of the sustained release effect of Gel-VH-EVs on diabetic mice wounds: 1 d, 2 d, 3 d and 4 d after the operation were selected as time nodes, and the mice were anesthetized again and placed in a small animal in vivo imager to detect the distribution and intensity of red fluorescence in the back wounds on both sides.

Figure 4:
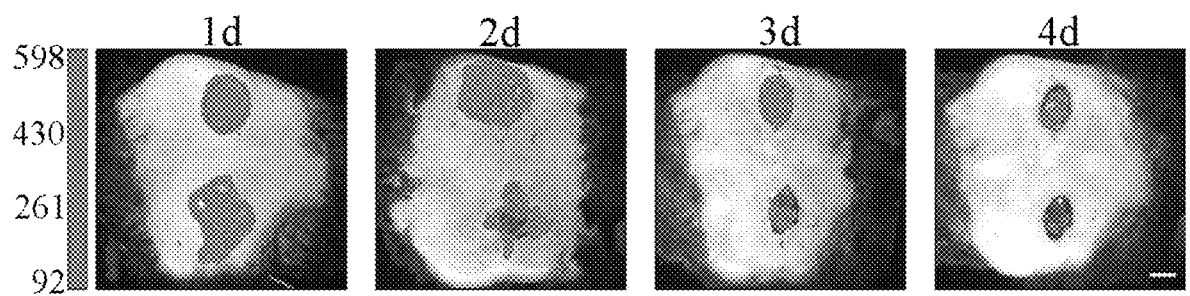
FIG. 4 shows distribution of exosomes released after the Gel-VH-EVs hydrogel in Example 2 is applied to a wound of one side of diabetic mice for 1 d, 2 d, 3 d and 4 d, with contralateral wounds being treated with a same amount of the free exosomes as a control.

After injection of free VH-EVs at the four points, fluorescence signals concentrated at the injection sites were difficult to spread, and were gradually cleared within 4 d. However, the VH-EVs released by the Gel-VH-EVs gel were evenly distributed on the wound surface and wound margin for a week, and still had a large amount of retention on the 4th day (FIG. 4). This phenomenon shows that the Gel-VH-EVs gel may play a sustained-release effect in mice to reduce the rapid clearance and degradation of VH-EVs, thereby increasing the bioavailability of VH-EVs and providing a more ideal way of administration, to avoid adverse reactions caused by repeated subcutaneous injections.

Example 3

In vivo use and therapeutic effect evaluation of Gel-VH-EVs prepared in Example 1

The mice used in this example were db/db mice with spontaneous type II diabetes for scientific research, which were purchased from SPF (Beijing) and had been approved by the Animal Ethics Committee.
1. Modeling: 60 eight-week-old male diabetic mice were randomly divided into 5 groups with 12 mice in each group. Anesthesia was conducted by injecting a 1% sodium pentobarbital solution intraperitoneally (at a dosage of 0.1 mL/20 g); operation was conducted as follows: after the anesthesia, the hair on the back of mice were removed, two positions 1 cm from a mid-spinal line on both sides of the back of mice were marked using a trephine puncher with a diameter of 10 mm, and full-thickness resection was conducted on the marked skin.
2. Postoperative administration: mice in a PBS group, an EVs group, and a VH-EVs group were subcutaneously injected with a microsyringe at the 3, 6, 9, and 12 o'clock positions of the wound margin on the postoperative day and every 2 d thereafter, where 12.5 μL of each group of drug solutions were injected at each point, for a total of 50 μL. A Gel-VH-EVs group and a GelMA group were added dropwise with 200 μL of (mixed solution without UV crosslinking) on each wound surface on the postoperative day with a disposable syringe, and quickly placed under UV light for fixating and crosslinking. In the Gel-VH-EVs, 15% VH-EVs had a concentration the same as that of EVs group and VH-EVs group.
3. Photographs and records: on the 4th, 8th and 12th day after the operation, the healing of all wounds of the mice in each group were observed and marked with a ruler, and photographed; a wound area was calculated using Image J software, and wound healing curves of the mice in each group were drawn.

Calculation according to a formula: wound healing rate=$(A0-At)/A0 \times 100\%$, in which, A0 was an initial area of the wound, and At was an actual wound area on an nth day.

Figure 5A:
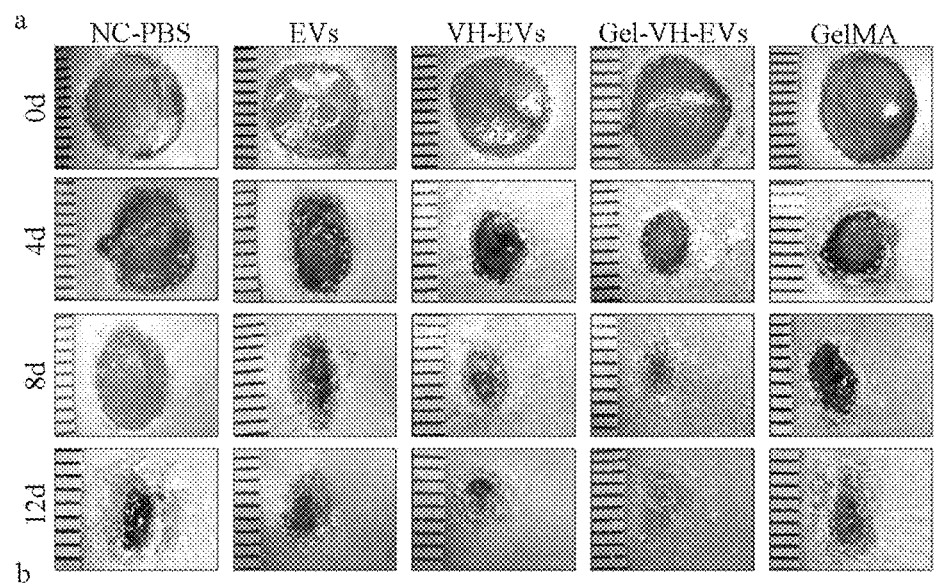
FIGS. 5a and 5b show an effect of promoting wound healing (a) and a statistical result of a wound healing rate (b) of the Gel-VH-EVs hydrogel in diabetic mice in Example 3.
Figure 5B:
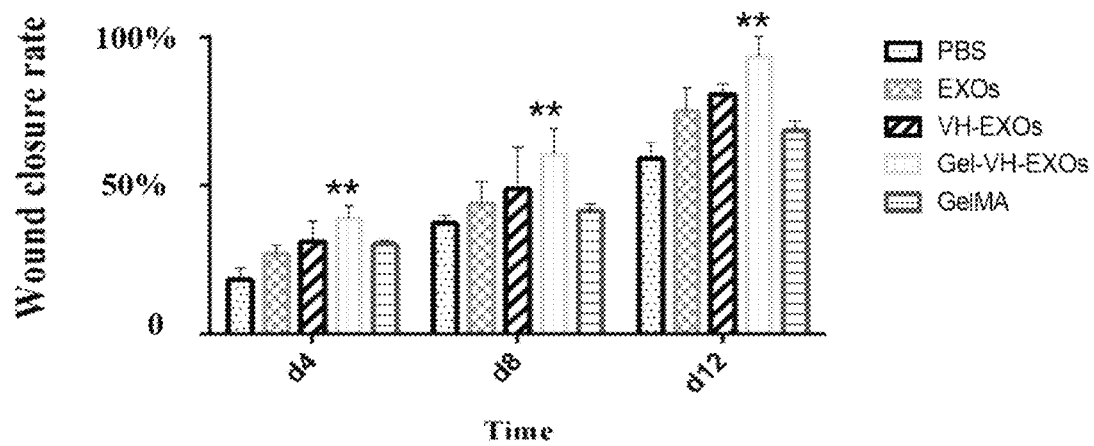

The wounds of the 5 groups of diabetic mice healed gradually over time, and the Gel-VH-EVs group had the minimum wound area at each time point; the healing rate of the VH-EVs group was higher than that of the EVs group and the GelMA group. There was no significant difference between the EVs group and the GelMA group. The diabetic mice in the PBS group had the lowest wound healing rate. After quantification according to the formula described in the method, it was found that Gel-VH-EVs treatment in each group could promote faster healing of diabetic wounds (FIGS. 5a and 5b), and the difference was statistically significant ($P<0.01$).

4. Blood perfusion analysis: the mice were anesthetized and placed under a laser Doppler blood flow monitor, and the blood flow perfusion on the wound surface was monitored by a 785 nm near-infrared laser. A probe was set at a uniform fixed distance of 10 cm from the wound surface, and a scanning window was set at 100 mm×100 mm. The back blood perfusion of each mouse was monitored and recorded.

Figure 6:
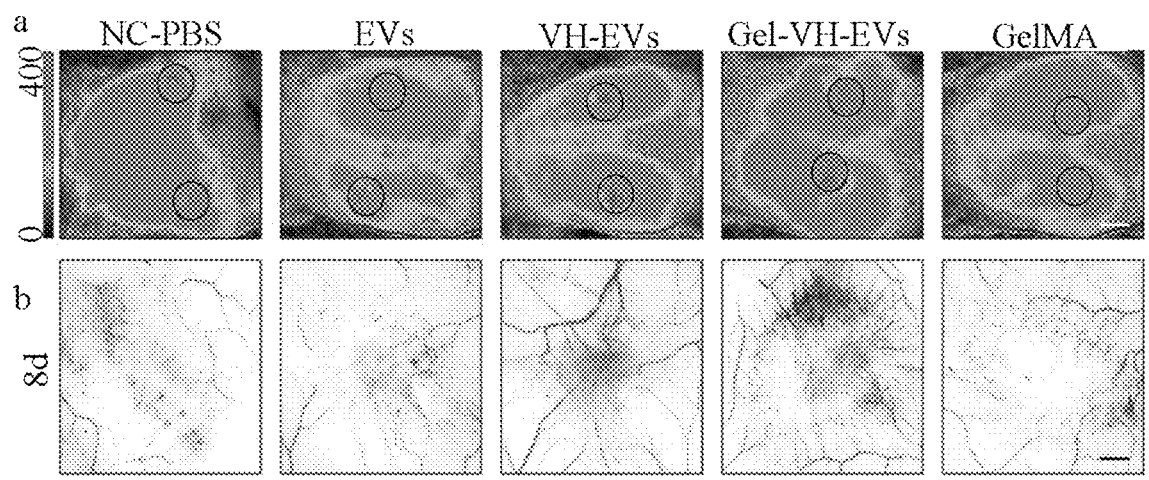
FIG. 6 shows a pro-angiogenesis effect of the Gel-VH-EVs hydrogel in Example 3 on wounds of diabetic mice, where a in FIG. 6 shows blood perfusion of the wounds, and b in FIG. 6 shows new blood vessels of the wounds.

The blood perfusion in back wounds of mice was observed by a laser Doppler blood flow detector. The area and color depth of the red area represented the intensity of blood perfusion at this location, and the condition of new blood vessels could be indirectly assessed therefrom. The results of average blood perfusion showed that the average blood perfusion of both sides of the wound in the Gel-VH-EVs group was significantly higher than that in the other groups, followed by the VH-EVs group; and the EVs group was higher than the PBS group and the GelMA group (a in FIG. 6).

5. Recording of new blood vessels: 8 d after operation, 3 mice in each group were sacrificed by cervical dislocation, and a circular incision was made at 1 cm from the wound margin with a center of the wound as a center of a circle, and the full-thickness skin of the mice was cut out. A subcutaneous side of the cut-out skin was quickly attached to a portable dermoscope, and angiogenesis on the wound surface and around the wound margin were observed and recorded after focusing.

The number and density of microvessels growing toward the wound margin in the skin tissue of each group of mice were observed by the portable dermoscope. In Gel-VH-EVs-treated mice, dense new capillaries were evenly distributed in the wound area; among the other groups, the VH-EVs group had relatively more new blood vessels, with uneven distribution; and in the remaining groups, the new blood vessels were relatively sparse and scattered (b in FIG. 6).

The above descriptions are merely preferred embodiments of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A method for preparing a photocurable hydrogel loaded with (1-cyanocyclopropane-1-carboxamido)-3,3-dimethylbutanoyl)-4-hydroxy-N-(4-(4-methylthiazol-5-yl)benzyl) pyrrolidine-2-carboxamide (VH298)-modified exosome, the method comprising the following steps:
1) Introducing VH298 into an exosome to obtain a VH298-modified exosome; and
2) Mixing the VH298-modified exosome obtained in step 1) with a hydrogel, and conducting an ultraviolet crosslinking to obtain the photocurable hydrogel loaded with VH298-modified exosome.

2. The method according to claim 1, wherein in step 1), a cell source of the exosome comprises one or more of a stem cell, a human embryonic kidney (HEK) 293 cell, a fibroblast, and an endothelial cell.

3. The method according to claim 1, wherein in step 1), a method for introducing the VH298 into the exosome specifically comprises: mixing a phosphate-buffered saline (PBS) solution of the exosome with the VH298, treating an obtained incubation solution by one of an electric shock method, a co-incubation method, and a cyclic freeze-thaw method, subjecting a treated incubation solution to solid-liquid separation, and collecting a solid phase.

4. The method according to claim 3, wherein the electric shock method comprises: subjecting the incubation solution to an electric shock in a square wave mode at a voltage of 1,000 V and a pulse of 1 ms, with an electrode plate spacing of 0.4 cm.

5. The method according to claim 3, wherein the co-incubation method comprises: conducting incubation on the incubation solution in a water bath at 36° C. to 38° C. for 1 h to 1.2 h in the dark.

6. The method according to claim 3, wherein the cyclic freeze-thaw method comprises: treating the incubation solution in liquid nitrogen for 2 min to 3 min and then at 36° C. to 38° C. for 2 min to 3 min successively, and conducting 3 cycles of freeze-thaw treatment.

7. The method according to claim 1, wherein the VH298-modified exosome and the hydrogel have a volume ratio of 1:10 to 1:20; and
wherein the hydrogel is a PBS solution comprising gelatin methacryloyl (GelMA) hydrogel with a mass concentration of 5% to 15% and a lithium Phenyl-2,4,6-trimethylbenzoylphosphinate (LAP) photoinitiator with a mass concentration of 0.2% to 0.3%.

8. The method according to claim 1, wherein the ultraviolet crosslinking is conducted at a wavelength of 405 nm for 8 sec to 12 sec.

9. A photocurable hydrogel loaded with VH298-modified exosome prepared by the method according to claim 1.

10. A method for repairing wound vascule, comprising administering to a patient in need thereof the photocurable hydrogel loaded with VH298-modified exosome according to claim 9.

11. The method according to claim 8, wherein in step 1), a cell source of the exosome comprises one or more of a stem cell, a HEK293 cell, a fibroblast, and an endothelial cell.

12. The method according to claim 8, wherein in step 1), a method for introducing the VH298 into the exosome specifically comprises: mixing a phosphate-buffered saline PBS) solution of the exosome with the VH298, treating an obtained incubation solution by one of an electric shock method, a co-incubation method, and a cyclic freeze-thaw method, subjecting a treated incubation solution to solid-liquid separation, and collecting a solid phase.

13. The method according to claim 12, wherein the electric shock method comprises: subjecting the incubation solution to an electric shock in a square wave mode at a voltage of 1,000 V and a pulse of 1 ms, with an electrode plate spacing of 0.4 cm.

14. The method according to claim 12, wherein the co-incubation method comprises: conducting incubation on the incubation solution in a water bath at 36° C. to 38° C. for 1 h to 1.2 h in the dark.

15. The method according to claim 12, wherein in step 1), the cyclic freeze-thaw method comprises: treating the incubation solution in liquid nitrogen for 2 min to 3 min and then at 36° C. to 38° C. for 2 min to 3 min successively, and conducting 3 cycles of freeze-thaw treatment.

16. The method according to claim 8, wherein the VH298-modified exosome and the hydrogel have a volume ratio of 1:10 to 1:20; and
the hydrogel is a PBS solution comprising GelMA hydrogel with a mass concentration of 5% to 15% and a LAP photoinitiator with a mass concentration of 0.2% to 0.3%.

17. The photocurable hydrogel according to claim 9, wherein in step 1), a cell source of the exosome comprises one or more of a stem cell, a HEK293 cell, a fibroblast, and an endothelial cell.

18. The photocurable hydrogel according to claim 9, wherein in step 1), a method for introducing the VH298 into the exosome specifically comprises: mixing a phosphate-buffered saline (PBS) solution of the exosome with the VH298, treating an obtained incubation solution by one of an electric shock method, a co-incubation method, and a cyclic freeze-thaw method, subjecting a treated incubation solution to solid-liquid separation, and collecting a solid phase.

19. The photocurable hydrogel according to claim 9, wherein the electric shock method comprises: subjecting the incubation solution to an electric shock in a square wave mode at a voltage of 1,000 V and a pulse of 1 ms, with an electrode plate spacing of 0.4 cm.

20. The photocurable hydrogel according to claim 9, wherein the co-incubation method comprises: conducting incubation on the incubation solution in a water bath at 36° C. to 38° C. for 1 h to 1.2 h in the dark.

\* \* \* \* \*